US011092509B1

(12) United States Patent
Langley et al.

(10) Patent No.: US 11,092,509 B1
(45) Date of Patent: Aug. 17, 2021

(54) CONTAINER CONTENT MONITORING DEVICE AND SYSTEM (71) Applicant: DeTech, LLC, Hebron, CT (US)

(72) Inventors: Mark Langley, Hebron, CT (US); Richard Langley, Hebron, CT (US)

(73) Assignee: DETECH, LLC, Hebron, CT (US)

( * ) Notice: Subject to any disclaimer, the term of this patent is extended or adjusted under 35 U.S.C. 154(b) by 0 days.

(21) Appl. No.: 16/598,609

(22) Filed: Oct. 10, 2019

Related U.S. Application Data (60) Provisional application No. 62/888,766, filed on Aug. 19, 2019.

(51) Int. Cl.
*G01M 3/32* (2006.01)
*G01K 3/00* (2006.01)
*G01G 23/18* (2006.01)
*G01N 33/00* (2006.01)
*G08B 25/10* (2006.01)
*G08B 21/18* (2006.01)
*G01K 1/024* (2021.01)
*H04L 29/08* (2006.01)

(52) U.S. Cl.
CPC .......... *G01M 3/3209* (2013.01); *G01G 23/18* (2013.01); *G01K 1/024* (2013.01); *G01K 3/005* (2013.01); *G01N 33/0047* (2013.01); *G08B 21/182* (2013.01); *G08B 25/10* (2013.01); *H04L 67/10* (2013.01)

(58) Field of Classification Search
CPC . G01M 3/3209; G01N 33/0047; G01K 1/024; G01K 3/005; G08B 25/10; G08B 21/182; G01G 23/18; H04L 67/10
See application file for complete search history.

(56) References Cited

U.S. PATENT DOCUMENTS

| 2013/0245991 | A1* | 9/2013 | Kriss ...................... F25D 29/003 702/150 |
| 2016/0131533 | A1* | 5/2016 | Parker ...................... G01K 1/14 374/150 |
| 2020/0072698 | A1* | 3/2020 | Baird, IV ............ G01M 3/3245 |

* cited by examiner

Primary Examiner — James J Yang
(74) Attorney, Agent, or Firm — McCormick, Paulding & Huber PLLC (57) ABSTRACT A container content monitoring system includes at least one container content monitoring device including a top plate connected to a housing, a weight sensor configured to detect a weight of an object arranged on the top plate, a temperature sensor configured to detect a temperature of the object where the object contacts the top plate, a transmitter, and a controller operatively connected to the temperature sensor, the weight sensor, and the transceiver. The transmitter may be configured to communicate with a cloud server remote from the container content monitoring device. The container content monitoring system further includes a router device configured to communicate with the at least one container content monitoring device, a cloud server remote from the at least one container content monitoring device, and a first user device configured to communicate with the cloud server.

16 Claims, 5 Drawing Sheets

| Name | Identifier 116 | Model # | Serial # | Manufacture (Or Put Into Service) Date | Repair Date | Certification Date | Calibrate Date | Tank Type | Tank Size | Alert Distribution Scheme | CCM System |
|---|---|---|---|---|---|---|---|---|---|---|---|
| 1004 | [barcode] | MLDT04 | ABC123 | XX/YY/ZZZZ | XX/YY/ZZZZ | XX/YY/ZZZZ | XX/YY/ZZZZ | Dewar – (of material type) | 25L | ·Alert 1- to user device 400A ·Alert 2- to all user devices 400 | 10 |

CONTAINER CONTENT MONITORING DEVICE AND SYSTEM

CROSS-REFERENCE TO RELATED APPLICATION

This application claims the benefit of U.S. Provisional Patent Application No. 62/888,766, filed Aug. 19, 2019, which is hereby incorporated by reference in its entirety.

BACKGROUND

Conventional container content monitoring devices and systems are used to monitor one or more parameters of contents contained within a container. Some conventional devices and systems use a temperature sensor arranged in the lid of the container to monitor a temperature of the contents.

There are drawbacks associated with conventional monitoring devices and systems. For example, devices and systems that use a temperature sensor to monitor the temperature of contents contained within the container may be subject to harsh conditions depending on the state of the contents. If the contents have a significantly high or low temperature, then the temperature sensor may be required to have a robust design to withstand repeated temperature changes and thermal stresses. Even with a robust design, the harsh temperature of the contents may lead to early failure of the temperature sensor, which may be unacceptable for the monitoring protocol of the container.

SUMMARY

A container content monitoring device in accordance with embodiments of the present disclosure includes a top plate connected to a housing, a weight sensor configured to detect a weight of an object arranged on the top plate, a temperature sensor configured to detect a temperature of the object where the object contacts the top plate, a transmitter, and a controller operatively connected to the temperature sensor, the weight sensor, and the transceiver. The transmitter may be configured to communicate with a cloud server remote from the container content monitoring device.

A container content monitoring system in accordance with embodiments of the present disclosure includes at least one container content monitoring device, each container content monitoring device of the at least one container content monitoring device including a top plate connected to a housing, a weight sensor configured to detect a weight of an object arranged on the top plate, a temperature sensor configured to detect a temperature of the object where the object contacts the top plate, a transmitter, and a controller operatively connected to the temperature sensor, the weight sensor, and the transceiver. The container content monitoring system in accordance with embodiments of the present disclosure further includes a router device configured to communicate with the at least one container content monitoring device, a cloud server remote from the at least one container content monitoring device, and a first user device configured to communicate with the cloud server. The transmitter may be configured to communicate with the cloud server.

DETAILED DESCRIPTION

Figure 1:
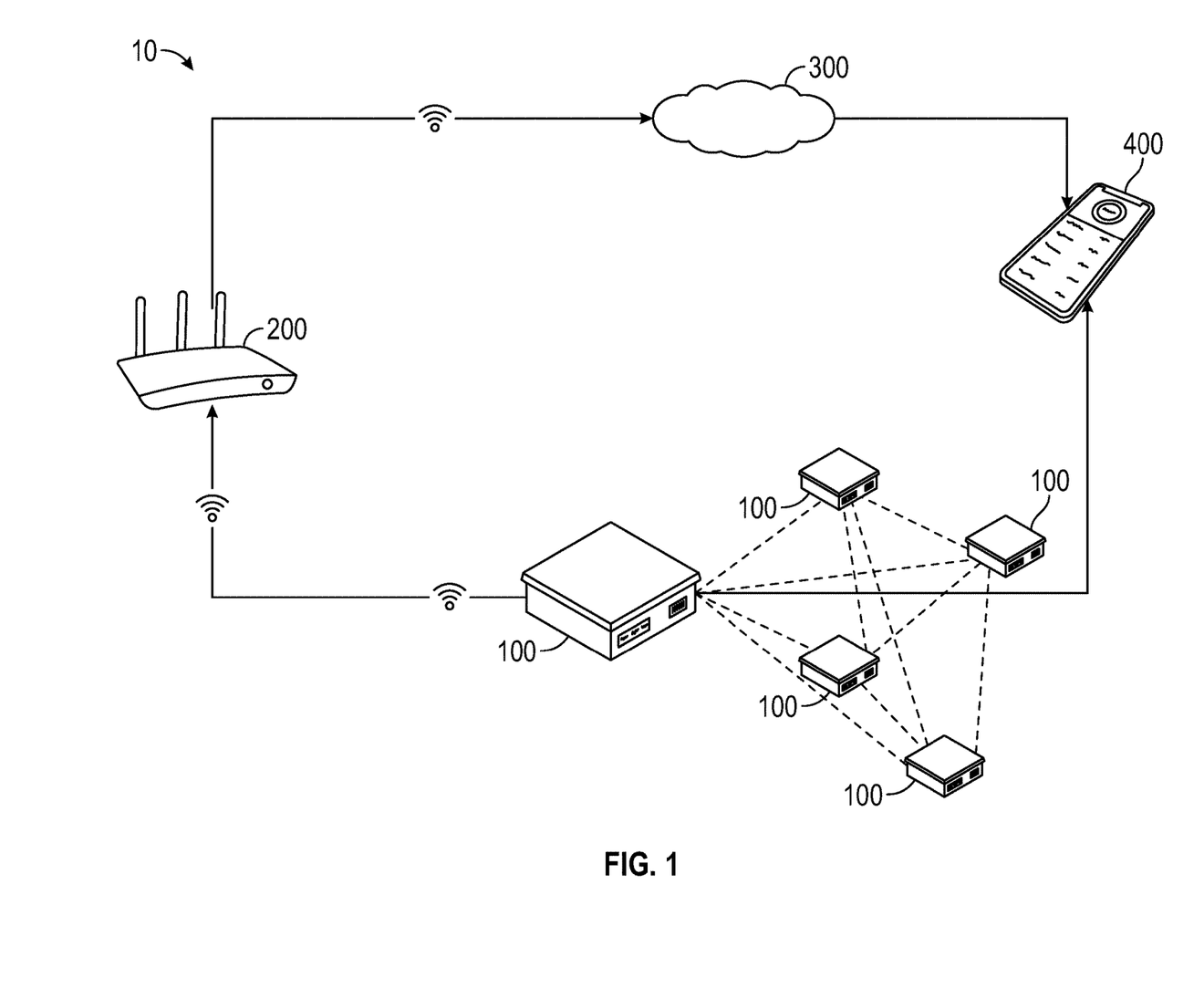
FIG. 1 is a diagram of a container content monitoring system in accordance with embodiments of the present disclosure.

Referring to FIG. 1, an exemplary container content monitoring ("CCM") system 10 includes a plurality of CCM devices 100, a gateway (or router device) 200, a cloud server 300 and a user device 400. The CCM devices 100 are configured to wirelessly communicate with the gateway 200. The gateway 200 is configured to wirelessly communicate with the cloud server wired or wirelessly 300. The cloud server 300 is configured to wirelessly communicate with the user device 400. The plurality of CCM devices 100 are optionally configured to communicate directly with the user device 400. The CCM devices 100, gateway 200, cloud server 300 and user device 400 are all remote from each other.

Referring to FIGS. 2A-2D, an exemplary CCM device 100 is shown in accordance with embodiments of the present disclosure. The CCM device 100 includes a top plate 102 connected to a top of a housing 104. A controller 106 is arranged within the top plate 102 and/or housing 104 and is operatively connected to a weight sensor 108, a temperature sensor 110 and a transceiver 112. A display screen 114 is optionally included as a part of the housing 104 and is operatively connected to the controller 106. The weight sensor 108 is arranged within or on the top plate 102 and/or housing 104 and is configured to measure (or detect) the weight of a container (or other object) placed on top of the top plate 102. The temperature sensor 110 is arranged within, on and/or under the top plate 102, housing 104 and/or an external surface mount of the container 500 and is configured to measure (or detect) a temperature of a container (or other object) placed on top of the top plate 102 where the container (or object) contacts the top plate 102. In some embodiments, the temperature sensor 110 is arranged to measure (or detect) a temperature of the container 500 or surface mount of the container 500 at a portion that does not contact the top plate 102. The transceiver 112 is configured to send and/or receive signals to and/or from the cloud server 300, which is discussed in greater detail below herein.

The CCM device 100 further includes an identifier 116. In one embodiment, the identifier 116 is a bar code and has a paired identifier bar code provided to the end user to be attached to the container 500 to assure the CCM device 100 and container 500 are matched during the life cycle of the CCM device 100 and container 500.

The weight sensor 108 is centrally located with respect to the top plate 102 and may be composed of a singular load cell or a group of load cells that come into direct or indirect contact with the underside of top plate 102 and housing 104, the load cell(s) being configured in such a way as to singularly and/or collectively calculate the weight of the container 500 with respect to the top plate 102. The temperature sensor(s) 110 is located at a distance from the center of the top plate 102. The temperature sensor(s) is integrated in such a way as to provide temperature monitoring of the top plate 102 and/or is in direct contact with target container 500. In some embodiments, it may be preferable to switch the positions of the weight sensor 108 and the temperature sensor 110, or to have both sensors 108, 110 centrally located with respect to the top plate 102, or to have both sensors arranged away from the center of the top plate 102 depending on the desired configuration. The desired configuration may be based on the size and shape of the container (or other object) to be placed on the CCM device 100.

Figure 2A:
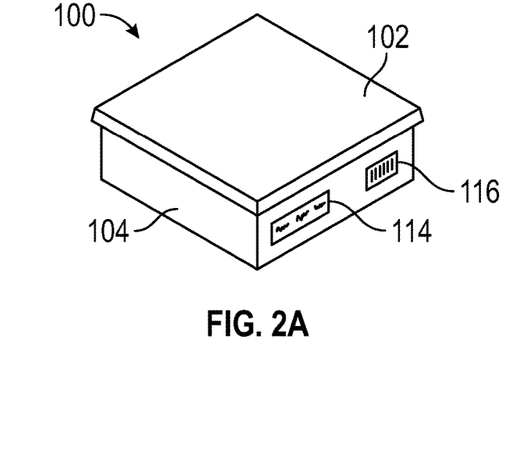
FIG. 2A is a top, front and left perspective view of a container content monitoring device in accordance with embodiments of the present disclosure.
Figure 2B:
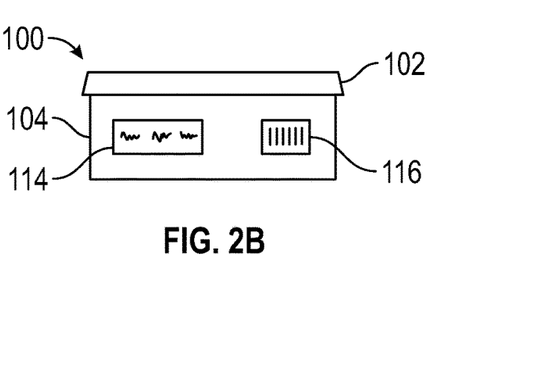
FIG. 2B is a front view of the container content monitoring device of FIG. 2A in accordance with embodiments of the present disclosure.
Figure 2C:
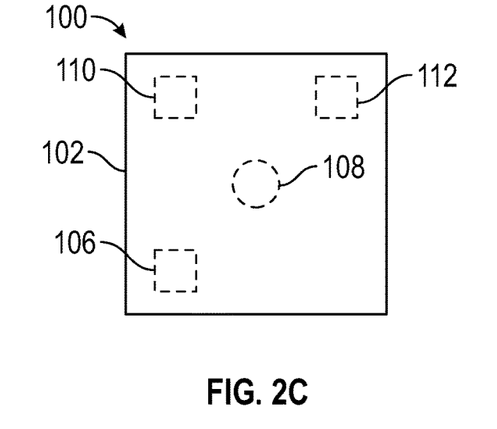
FIG. 2C is a top view of the container content monitoring device of FIG. 2A in accordance with embodiments of the present disclosure.
Figure 2D:
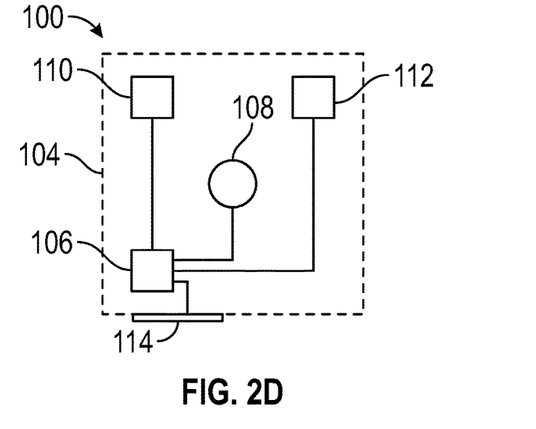
FIG. 2D is a schematic view of components of the container content monitoring device of FIG. 2A in accordance with embodiments of the present disclosure.

Based on signals from the controller 106, the display screen 114 is configured to display a weight value (or weight data) as measured by the weight sensor 108. The weight value may be displayed in one or more units, such as kilograms and/or pounds. The controller 106 is configured to optionally perform a tare function to set the recognized weight value at the weight sensor 108 to zero when the tare function is performed. Based on signals from the controller 106, the display screen 114 is configured to display a temperature value (or temperature data) as measured by the temperature sensor 110. The temperature value may be displayed in one or more units, such as Fahrenheit, Celsius, and/or Kelvin. The controller 106 is configured to monitor and record the weight data and temperature data continuously, intermittently or periodically.

Figure 3A:
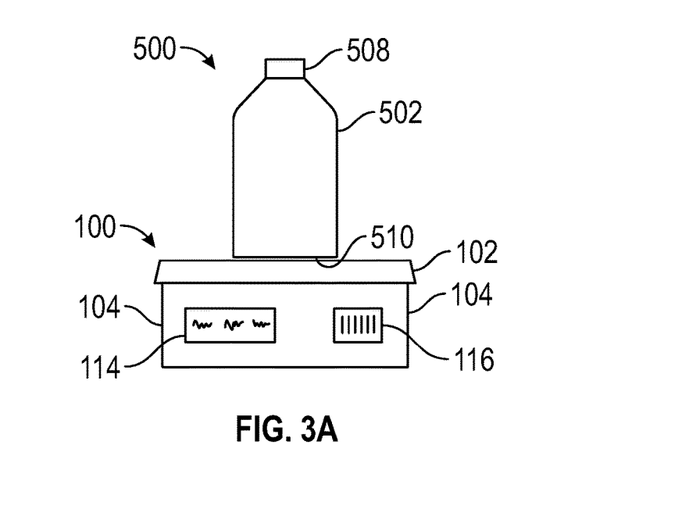
FIG. 3A is a front view of the container content monitoring device of FIG. 2A with a container arranged thereon in accordance with embodiments of the present disclosure.
Figure 3B:
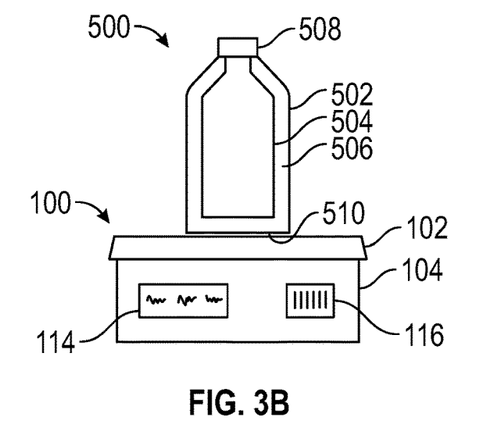
FIG. 3B is a front view of the container content monitoring device with the container arranged thereon of FIG. 3A, the container being transparently illustrated, in accordance with the embodiments of the present disclosure.
Figure 3C:
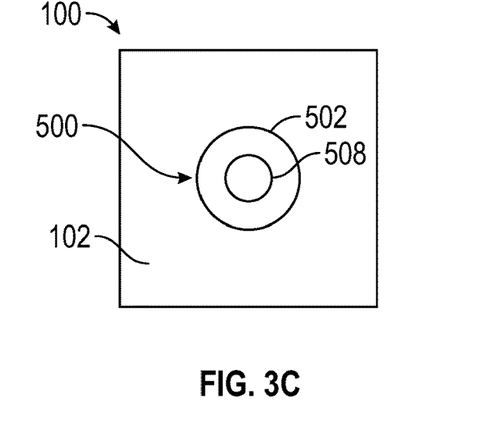
FIG. 3C is a top view of the container content monitoring device with the container arranged thereon of FIG. 3A in accordance with embodiments of the present disclosure.

Referring to FIGS. 3A-3C, the CCM device 100 of FIG. 2A is shown with a Dewar type container 500 arranged thereon. The Dewar container 500 includes an outer body 502, an inner body 504, and a space 506 between the outer body 502 and the inner body 504 that is vacuum sealed. The inner body 504 is configured to store contents therein. A lid 508 is provided at the top of the container 500 to seal the inner body 504, and any contents stored therein. A bottom 510 of the container 500 is in contact with the top of the top plate 102 of the CCM device 100.

The CCM device 100 is configured to continuously, intermittently or periodically monitor the temperature of the bottom 510 of the container 500 through measurement (or detection) with the temperature sensor 110. Similarly, the CCM device 100 is configured to continuously, intermittently or periodically monitor the weight of the container 500 and its contents through measurement (or detection) with the weight sensor 108. The controller 106 is configured to compare the obtained weight data with a predefined threshold, such as a low threshold, high threshold, and/or rate of change threshold. Similarly, the controller 106 is configured to compare the obtained temperature data with a low threshold, a high threshold, and/or a rate of change threshold. The CCM device 100 is also configured to generate and distribute alerts after a comparison of the weight data and/or temperature data being determined as exceeding a threshold. For example, an alert may be generated if the temperature data decreases below or increases above (or outside) a low temperature threshold or the weight data decreases below or above (or outside) a low weight threshold. As an alternative to the predefined threshold, or in addition thereto, the CCM device 100 can be configured to compare the weight data and/or temperature data with one or more dynamic thresholds that are set based on certain current conditions (or measured parameters), such as the weight of the contents/container, the room temperature, time of day, and the like. The thresholds can also be configured to the size container 500 and/or the quantity, mass, or volume of contents to be stored therein.

In some embodiments, a decreased temperature reading at the bottom 510 of the container 500 may indicate that the vacuum seal of the space 506 has been broken. Since the laws of thermodynamics do not provide for the thermal transfer of heat energy between two objects separated by a vacuum via conduction or convection, the thermal integrity of container 500 is substantially maintained if a hermetically sealed vacuum is maintained between the outer wall 502 and the inner wall 504. As soon as the vacuum in the space 506 is compromised, either gradually or in a single instant the thermodynamic properties between surfaces 502 and 504 will allow thermal transfer thus resulting in gradual or dramatic loss of contents, which may result in a change in temperature of surface 502. In the event a vacuum in the space 506 is compromised due to failure of outer wall surface 502, no contents will enter the space 506 and the drop in temperature of surface 502 will be gradual or rapid depending upon the vacuum remaining in space 506. In the event a vacuum in the space 506 is compromised due to failure of inner wall surface 504, then contents may enter the space 506 depending upon the liquid level within the container 500 and the levels of contents in the container 500 respectively. Should contents enter the space 506 resulting in a rapid temperature change of the temperature of the bottom 510 of the container 500 and/or a rapid weight loss, one or both may be recorded by the CCM device 100 in real time.

For example, the vacuum seal of the space 506 may be broken when the inner body 504 of the container 500 has been breached or damaged and the contents of the container 500 may enter the space 506 and come into contact with the bottom 510 and/or outer body 502 of the container 500. If the contents were, e.g., a cryogenic substance such as liquid nitrogen, the breach and resulting flow of liquid nitrogen into the space 506 could cause the obtained temperature data to decrease below or above (or outside) a predefined low temperature threshold. In some embodiments, the lid 508 may not be properly engaged with the body 502, which could lead to escape of the contents stored in the inner body 504 through the unsealed lid 508 by known processes, such as evaporation, sublimation, and the like, which could eventually cause the obtained weight data to decrease below or above (or outside) a predefined low weight threshold.

Figure 4A:
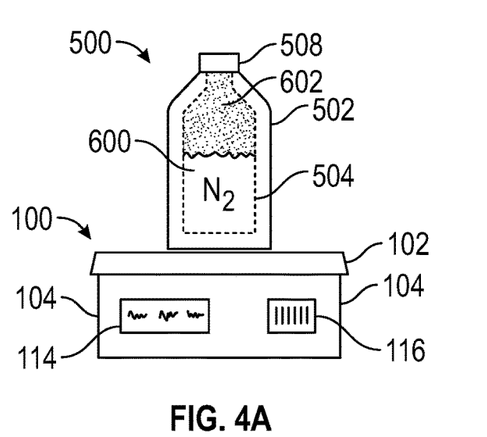
FIG. 4A is a front view of the container content monitoring device of FIG. 2A with a container arranged thereon containing liquid nitrogen in accordance with embodiments of the present disclosure.
Figure 4B:
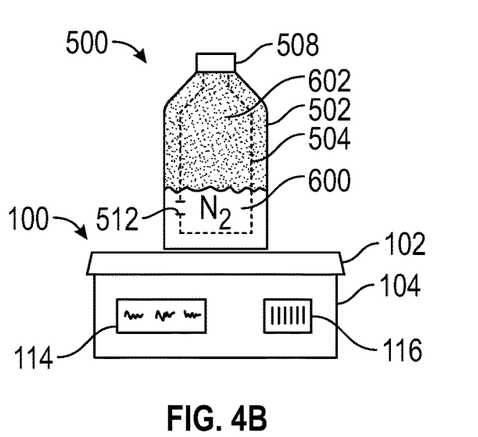
FIG. 4B is a front view of the container content monitoring device with the container arranged thereon of FIG. 4A with a breach in the container in accordance with embodiments of the present disclosure.

In the embodiment shown in FIGS. 4A and 4B, the Dewar flask 500 contains liquid nitrogen 600 as well as gaseous nitrogen 602. FIG. 4B shows one type of breach 512 possible in the inner body 504, which results in the liquid nitrogen 600 and/or gaseous nitrogen 602 entering the space 506. In some embodiments, a decreased weight reading detected by the weight sensor 108 indicates that too much nitrogen has evaporated or escaped from the container 500 and the liquid nitrogen must be replaced or the Dewar flask 500 be repaired or replaced. While the breach 512 is shown as being located where the liquid nitrogen 600 is arranged, a breach could also occur above the level of the liquid nitrogen 600, i.e. where the gaseous nitrogen 602 is arranged. The CCM device 100 is configured to detect a breach no matter where the breach is located.

The CCM device 100 may be configured to generate and distribute alerts having different levels of importance or urgency. In some embodiments, the obtained weight or temperature data being beyond a first threshold may correspond to a first warning alert, and obtained weight or temperature data being beyond a second threshold may correspond to a second warning alert, the second warning alert being more important or urgent than the first warning alert. In some embodiments, the type of alert could also be based on two parameters being beyond a threshold, such as the weight and temperature being beyond a first and/or second threshold (or a "multi-parameter alert").

Figure 5:
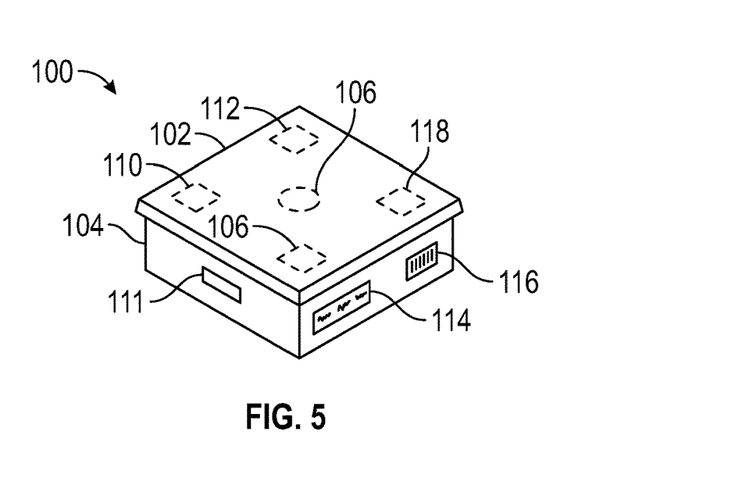
FIG. 5 is a top, front and left perspective view of a container content monitoring device in accordance with embodiments of the present disclosure.

Referring to FIG. 5, the CCM device 100 is equipped with an optional room temperature sensor (or second temperature sensor) 111. The room temperature sensor 111 is configured to measure (or detect) the ambient temperature of the environment of the CCM device 100. The room temperature sensor 111 may be arranged on a different side of the CCM device 100 than the temperature sensor 110 configured to measure the temperature of the bottom of the container 510, e.g. the room temperature sensor 111 may be arranged on the side or bottom of the CCM device 100. The room temperature data allows the controller 106 to compare obtained room temperature data from the room temperature sensor 111 with obtained temperature data of the bottom 510 of the container 500 obtained from the temperature sensor 110 without being influenced by temperature changes associated with the bottom of the container 510 (or at least not as influenced as the temperature sensor 110), as discussed above.

The CCM device 100 includes an optional volatile organic compound ("VOC") detector 118 operatively connected to the controller 106. The VOC detector 118 allows remote and/or local monitoring of ambient VOCs. In embodiments where the container 500 contains VOCs, the VOC detector 118 can detect leaks from the container 500. This advantageously provides an additional monitoring parameter to the weight and temperature parameters.

Figure 6:
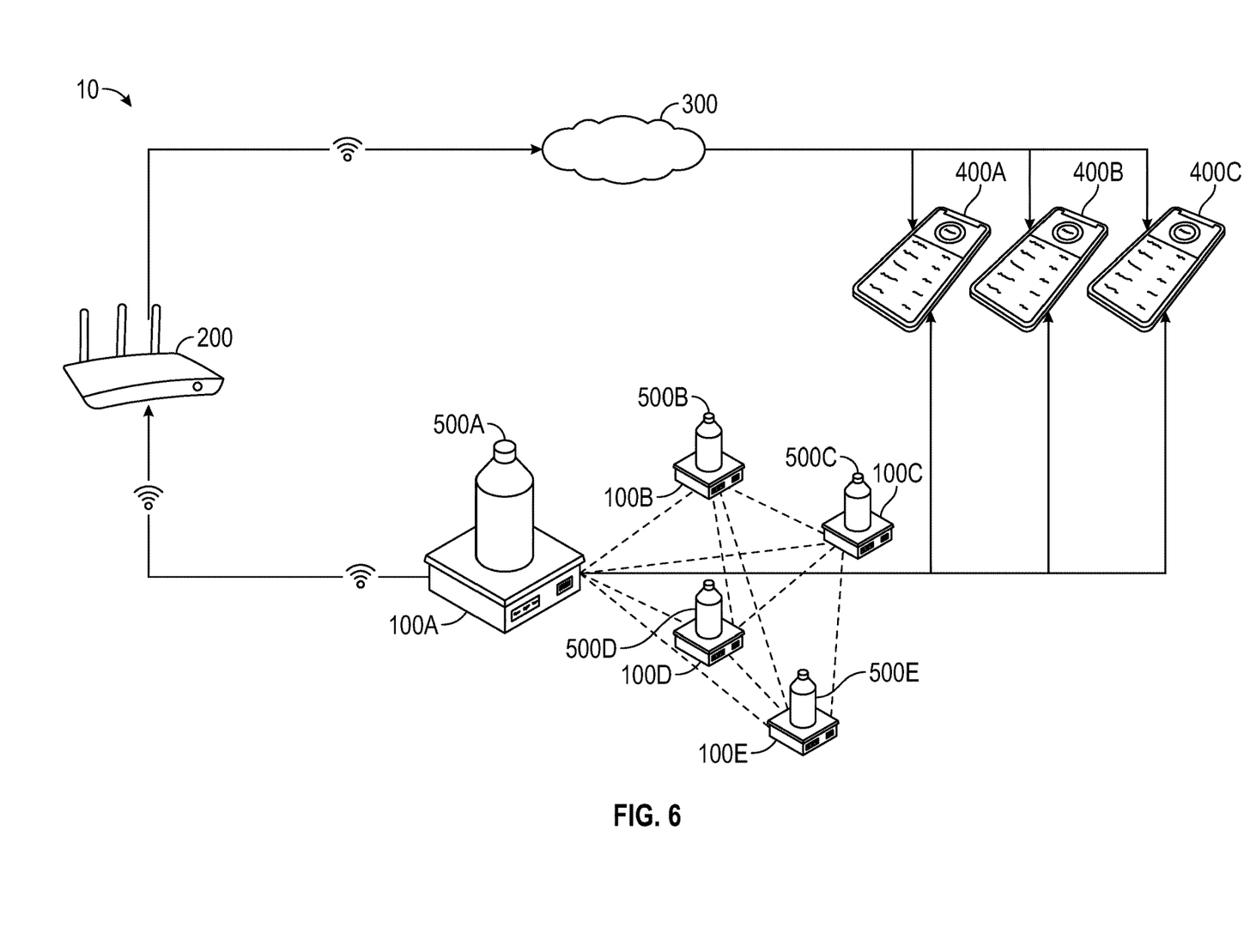
FIG. 6 is a diagram of a container content monitoring system in operation in accordance with embodiments of the present disclosure.

Referring to FIG. 6, a CCM system 10 is shown in operation in accordance with embodiments of the present disclosure. The CCM system 10 is substantially similar as the CCM system of FIG. 1, except that this system 10 comprises a plurality of user devices 400A, 400B, 400C (collectively 400). Otherwise, the system 10 contains similar elements and features as discussed above.

Each CCM device 100A, 100B, 100C, 100D, 100E (collectively 100) has a Dewar flask type container 500A, 500B, 500C, 500D, 500E (collectively 500) arranged thereon. Several of the containers 500A, 500B, 500C may be 25 liter (L) size containers and several of the containers 500D, 500E may be 75 liter (L) size containers. Each container 500 contains liquid nitrogen and gaseous nitrogen. The CCM devices 100 monitor the weight of the containers 500 using respective weight sensors and the temperature of the bottom of the containers using respective temperature sensors as discussed above. The data collected is sent to a router device 200, which delivers the data to the cloud server 300. When desired, a user could operate one of the user devices 400 to access the cloud server 300 in order to obtain a status report of the monitored containers 500.

Even when a user is not accessing the cloud server 300, the CCM devices 100 are monitoring the containers 500. In one scenario, once the weight data in the container 500A is determined to exceed a first low weight threshold (refill limit), the CCM device 100A delivers an alert to the cloud server 300. The cloud server 300 distributes the alert to the plurality of user devices 400 that the container 500A is malfunctioning. In another scenario, the weight data in the container 500B may be determined to not exceed a first low weight threshold, but the rate of change of the weight data is determined to exceed a first rate of change threshold. The cloud server 300 distributes the alert to the plurality of user devices 400 that the container 500B is malfunctioning. Users of the user devices can take appropriate action following receipt of the alert(s).

In some embodiments, the alert may be delivered to a subset of the user devices 400 depending on the type of alert. For example, if a first low weight or temperature threshold is exceeded, the alert may be distributed to a single user device 400A. The single user device 400A may be a predetermined user device 400 or the user device(s) 400 that corresponds to a predetermined schedule depending on the time and/or date or day of the week, e.g. an "on-call schedule." The system 10 may also be configured to distribute the alert to all of the user devices 400 regardless of the predetermined schedule if the user of the predetermined user device 400A does not confirm receipt of the alert or if the weight or temperature data exceeds a second low weight or temperature threshold, indicating a more severe malfunction.

Figure 7:
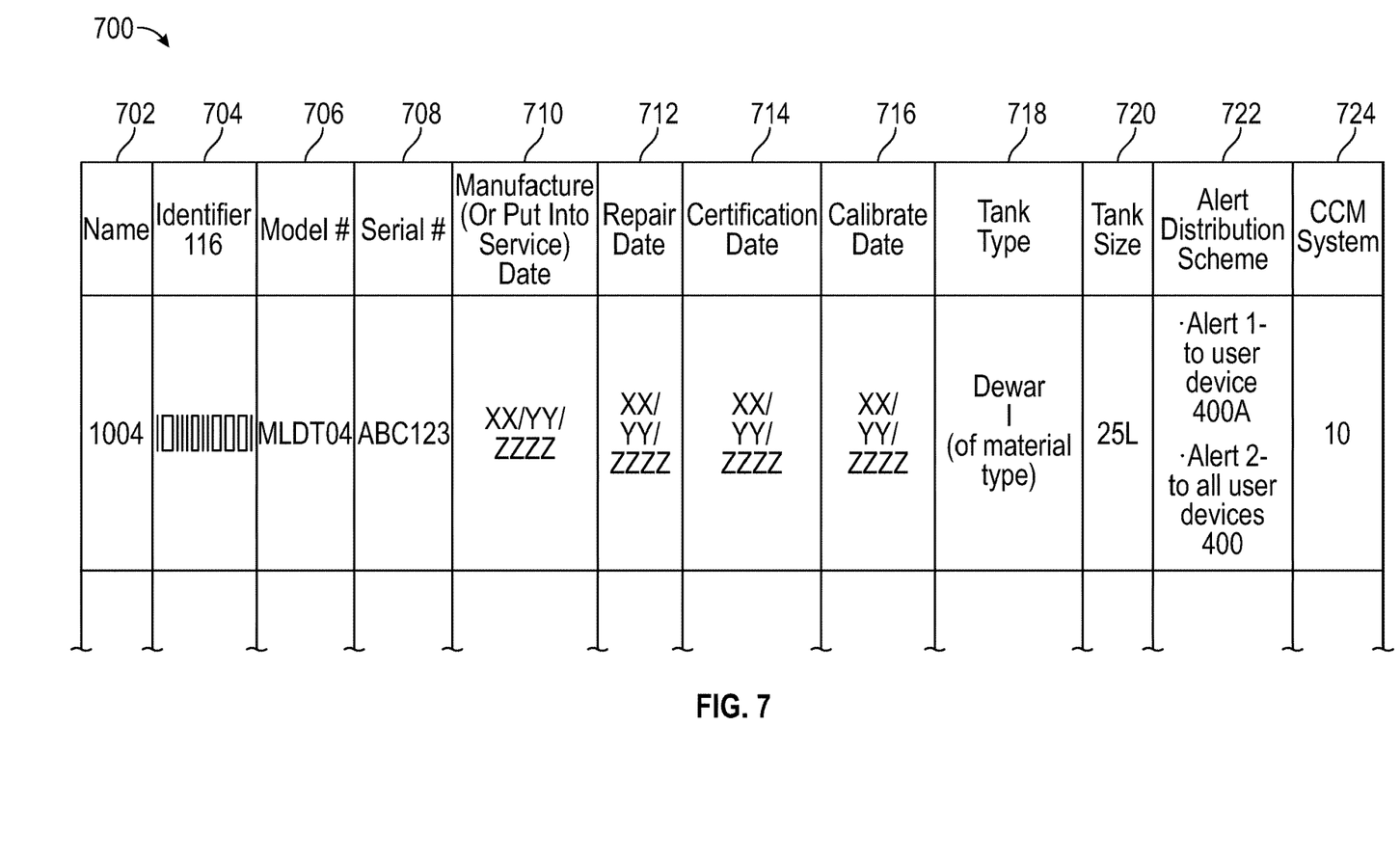
FIG. 7 is an inventory matrix in accordance with embodiments of the present disclosure.

Referring to FIG. 7, an exemplary inventory matrix 700 for storage on a cloud server 300 (or other device) is shown in accordance with embodiments of the present disclosure. The inventory matrix 700 is configured to store inventory information associated with one or more CCM systems 10 and/or CCM devices 100. The inventory information may comprise one or more of the following: custom names 702 of each of CCM device 100, the identifier 704 for each CCM device 100, the model number 706 of each CCM device 100, the serial number 708 of each CCM device 100, the date(s) each CCM device 100 was manufactured (or put into service) 710, repaired 712, certified 714, calibrated 716, and the like. The inventory matrix 700 may also include what tank type 718 and what tank size 720 each CCM device 100 is configured to monitor, which may indicate what type of thresholds the CCM device 100 is configured with. The inventory information may also include the alert distribution scheme 722 for each CCM device 100 depending on the alert, i.e. which user devices 400 are predetermined for receiving alerts for the CCM device 100. Instead of being associated with inventory information, the alert distribution scheme can be stored and utilized separately from the inventory information. Each CCM device 100 can be associated with a particular CCM system 10 in the CCM system column 724.

Advantageously, the systems and devices disclosed herein may be used in connection with storage facilities that use cryogenic storage containers to store embryos, sperm and oocytes. Such storage facilities could utilize the systems and devices herein to reliably monitor liquid nitrogen contents (or other cryogen substance) of the storage containers. In the event of a container failure, breach or improper lid securement, the systems and devices disclosed herein could distribute alerts to employees or contractors of the facility to address the container failure before the temperature in the container increased beyond a temperature that would cause damage to the stored embryos, sperm or oocytes. While the systems and devices may advantageously be used in cryogenic storage facilities, it is within the scope of the present disclosure for the systems and devices to be used in other facility types and to monitor other types of containers or objects storing different contents therein.

In some embodiments, the CCM device 100 is configured to communicate with one or more other CCM devices 100. In such a configuration, the CCM devices 100 are capable of comparing obtained temperature readings for analysis. For example, the obtained temperature readings can be averaged such that each obtained temperature reading is compared to the average in order to accurately compare the temperature of the bottom of a particular container with the ambient room temperature. The compared temperature readings can obtain measurements obtained by the temperature sensor 110 arranged to measure the temperature of the bottom 510 of the container 500 and/or the temperature sensor 111 arranged to measure the room temperature.

While the controller 106 has been described as performing the processing (or analysis) of the obtained weight and temperature data, it is within the scope of the present disclosure for the processing of the weight and temperature data (and VOC data) to be performed by a different processor remote from the controller 106 and CCM 100 device. For example, the controller 106 may function primarily to collect the data from the sensors and transmit the data to the cloud server 300 for remote processing. The controller 106 and/or the cloud server 300 may be configured to automatically distribute alerts to user devices in different forms, such as by text message, email, audio sounds, flashing lights, and the like. In some embodiments, the controller 106 and/or cloud server 300 may communicate with several user devices 400 through an application interface, which interface enables remote monitoring of parameters of the CCM device(s) 100. In addition to real-time mobile monitoring of parameters, the application interface allows alerts such as push notifications to be distributed to a user device if a certain set of parameters is recognized. In some embodiments, a telephone call tree may be used whereby the controller 106 and/or cloud server 300 causes successive telephone calls to user devices until a response or confirmation is received.

Additionally, the controller 106 and/or cloud server 300 may be in communication with a server enabling a web interface. Users would be able to achieve similar monitoring and identification functions as described above with respect to a mobile application by using the web interface.

The cloud server 300 may be configured to continuously, intermittently or periodically analyze the data collected by the CCM device(s) 100 in order to yield predictive information for predictive analytics. For example, the cloud server 300 could be configured to use the obtained weight and temperature data gathered over time to predict if one or more containers 500 is failing or has failed before an alert would otherwise be generated based on the thresholds. Based on identified patterns of evaporation rate of the contents of the container(s), the cloud server 300 could predict when one or more containers need to be refilled with additional contents and/or when the container(s) need to be replaced.

The predictive analytics model may begin functioning after any given container 500 has compiled ample data after a period of time, e.g. over a period of months, taking into account a frequency of access to any given tank 500 by the user, the average container temperature, the average ambient temperature and the rate at which normal evaporation takes place over a period of time during normal use. This establishes a threshold of acceptable operation parameters. Once the above normal averages are established for any given container 500, the CCM predictive analytics programming may predict a failure if one or more of the following takes place:

1 the loss of weight exceeds the normal average;
2 the external container 500 displays a colder than normal average temperature at surface 102 or other known stable temperature data logged area; and/or
3 the surface temperature of container 500 drops while the average ambient temperature remains constant.

The above combined data will allow CCM algorithms to predict there is a vacuum compromise and/or failure taking place based on deviations from an average weight loss over time or from an average temperature over time of the container 500.

Since the CCM algorithms take into account the frequency of container access, embodiments of CCM devices and systems according to the present disclosure may be configured to predict container failure whether the container has low usage (i.e. long-term storage with infrequent access) or for higher usage (i.e. more frequent access to container for addition/removal of items stored within the container, for sampling or for other purposes). The change in weight and/or temperature for low usage or higher usage container applications can be recognized by CCM devices and systems according to the present disclosure and be accounted for when determining container failures and/or distributing alerts.

In some embodiments, instead of distributing alerts to user devices for manual refilling of container contents, or in addition thereto, the controller 106 and/or cloud server 300 could be configured to cause a refilling device (not shown) to refill the container with the appropriate contents if an alert is generated due to one or more measured parameters exceeding one or more thresholds.

In some embodiments, the top plate 102 may be made of stainless steel or a hard plastic, such as ABS plastic, such that the top plate 102 is durable, washable, and/or non-porous.

In some embodiments, the identifier 116 may be placed on the front-right side of the housing 104 of the CCM device 100 for easy scanning and/or visibility. The display screen 114 may be placed on the front side of the device and display current obtained data, warnings, and/or alerts. The display 116 may be local or remote and may also be displayed on a user device 400 or other computer display.

It should be readily understood by those skilled in the art that the transceiver 112 may utilize one or more known forms of wireless communication, such as, for example and without limitation, WiFi, Bluetooth (e.g. Bluetooth 5.0), cellular or mobile communications networks, radio communication, near field communication, and/or the like. The transceiver 112 may communicate by use of a router, Bluetooth gateway, or other modem.

While the transceiver 112 has been shown and described herein as being a wireless transceiver, it should be readily understood that wired transceivers may be used instead of a wireless transceiver (or in addition to) and are within the scope of the present disclosure. Further, the function of the transceiver 112 could be accomplished with a transmitter and receiver configuration. Moreover, any of the wireless communication described herein in connection with the other components could additionally or alternatively be accomplished with known wired communication technology. For example, the gateway 200 could be wired to the cloud server 300.

While the identifier 116 has been shown and described as being a bar code, it should be readily understood that any kind of identifier can be used instead of a bar code or in addition to a bar code. For example, the identifier can be, without limitation, a quick response code (i.e. a "QR" code; a 2-dimensional bar code type), a serial number, a radio frequency identification (RFID) tag, or a near field communication tag or smart tag.

It should be understood that any number of the disclosed elements or features are within the scope of the present disclosure. For example, in some CCM systems there may be a single CCM device 100, or multiple gateways 200, server clouds 300 and/or user devices 400.

While the various components of the CCM system 10 and the CCM device 100 have been shown in particular locations or relative spatial positioning, it should be readily understood that virtually any other configuration or arrangement is within the scope of the present disclosure to achieve the functions and purposes described herein.

It is within the scope of the present disclosure to monitor the contents of any type or size of object or container. Accordingly, the container could be made of any material and could have any lid mechanism without the need to have a temperature sensor arrangement be installed in the lid. Thus, temperature sensors of the CCM systems and devices of the present disclosure may advantageously avoid the wear or damage associated with the removal or mounting of a lid with an object or container.

While embodiments of the present disclosure have been shown and described for monitoring containers containing liquid nitrogen, embodiments for monitoring containers containing other elements or compounds are within the scope of the present disclosure.

The present disclosure advantageously describes a CCM system 10 and CCM device 100 that can be suitably modified for a wide range of content monitoring applications. Thus, embodiments in accordance with the present disclosure are advantageously scalable in size and material types to achieve the particular objectives.

While the present disclosure has been illustrated and described with respect to particular embodiments thereof, it should be appreciated by those of ordinary skill in the art that various modifications to this disclosure may be made without departing from the spirit and scope of the present disclosure.

What is claimed is:

1. A container content monitoring device comprising: a housing having a top plate;
    a weight sensor configured to detect a weight of an object disposed on the top plate;
    a temperature sensor configured to detect a temperature of the object placed on the top plate at an external surface of the object;
    a transmitter associated with the housing; and
    a controller operatively connected to the temperature sensor, the weight sensor, and the transmitter;
    wherein the transmitter is configured to communicate with a cloud server remote from the container content monitoring device;
    wherein the controller is configured to generate a first low weight warning alert when the weight sensor detects the weight of the object as being below or above a first predefined weight threshold, indicating that the object has failed, has been breached, or has improper lid securement; and
    wherein the controller is configured to generate a first low temperature warning alert when the temperature sensor detects the temperature of the object where the object contacts the top plate as being below or above a first predefined temperature threshold, indicating that the object has failed, has been breached, or has improper lid securement.

2. The container content monitoring device according to claim 1, wherein the object arranged on the top plate is a container.

3. The container content monitoring device according to claim 2, wherein the container is a Dewar type container.

4. The container content monitoring device according to claim 1, wherein the transmitter is a transceiver.

5. The container content monitoring device according to claim 1, wherein the controller is configured to record the weight of the object detected by the weight sensor over time as weight data, wherein the controller is configured to determine a rate of change of the weight data, and wherein the controller is configured to generate a first high rate of weight change warning alert when rate of change of the weight data exceeds a first predefined rate of weight data change threshold.

6. The container content monitoring device according to claim 1, wherein the controller is configured to record the temperature of the object where the object contacts the top plate as detected by the temperature sensor over time as temperature data, wherein the controller is configured to determine a rate of change of the temperature data, and wherein the controller is configured to generate a first high rate of temperature change warning alert when rate of change of the temperature data exceeds a first predefined rate of temperature data change threshold.

7. The container content monitoring device according to claim 1, wherein the controller is configured to generate a multi-parameter alert when the weight sensor detects the weight of the object as being below or above a first predefined weight threshold and when the temperature sensor detects the temperature of the object where the object contacts the top plate as being below or above a first predefined temperature threshold.

8. The container content monitoring device according to claim 1, further comprising a volatile organic compound detector configured to monitor a level of ambient volatile organic compounds, wherein the volatile organic compound detector is in operative connection with the controller.

9. The container content monitoring device according to claim 1, wherein the transmitter is configured to communicate with the cloud server through a router device remote from the container content monitoring device.

10. The container content monitoring device according to claim 1, further comprising a room temperature sensor configured to detect a temperature of the environment of the container content monitoring system, wherein the controller is operatively connected to the room temperature sensor.

11. A container content monitoring system comprising:
at least one container content monitoring device, each container content monitoring device of the at least one container content monitoring device comprising:
a top plate connected to a housing;
a weight sensor configured to detect a weight of an object arranged on the top plate;
a temperature sensor configured to detect a temperature of the object at an external surface where the object contacts the top plate;
a transmitter; and
a controller operatively connected to the temperature sensor, the weight sensor, and the transmitter;
a router device configured to communicate with the at least one container content monitoring device;
a cloud server remote from the at least one container content monitoring device; and
a first user device configured to communicate with the cloud server;
wherein the transmitter is configured to communicate with the cloud server;
wherein the controller is configured to generate a first low weight warning alert when the weight sensor detects the weight of the object as being below a first predefined weight threshold, indicating that the object has failed, has been breached, or has improper lid securement, and wherein the controller is configured to distribute the first low weight warning alert to the cloud server through the router device; and
wherein the controller is configured to generate a first low temperature warning alert when the temperature sensor detects the temperature of the object where the object contacts the top plate as being below or above a first predefined temperature threshold, indicating that the object has failed, has been breached, or has improper lid securement, and wherein the controller is configured to distribute the first low temperature warning alert to the cloud server through the router device.

12. The container content monitoring system according to claim 11, further comprising a plurality of container content monitoring devices, the at least one container content monitoring device being one of the plurality of container content monitoring devices.

13. The container content monitoring system according to claim 11, further comprising a plurality of user devices, the first user device being one of the plurality of user devices.

14. The container content monitoring system according to claim 11, wherein the controller is configured to generate a multi-parameter alert when the weight sensor detects the weight of the object as being below or above a first predefined weight threshold and when the temperature sensor detects the temperature of the object where the object contacts the top plate as being below or above a first predefined temperature threshold, and wherein the controller is configured to distribute the multi-parameter warning alert to the cloud server through the router device.

15. The container content monitoring system according to claim 11, wherein the cloud server has an inventory matrix stored therein, the inventory matrix comprising information associated with the at least one container content monitoring device.

16. The container content monitoring system according to claim 11, wherein the first user device is configured to communicate with the at least one container content monitoring device.

* * * * *